(12) United States Patent
Lindkvist

(10) Patent No.: US 10,758,691 B2
(45) Date of Patent: Sep. 1, 2020

(54) ADDITIVE GAS DELIVERY APPARATUS

(71) Applicant: MAQUET CRITICAL CARE AB, Solna (SE)

(72) Inventor: Leif Lindkvist, Bromma (SE)

(73) Assignee: Maquet Critical Care AB, Solna (SE)

( * ) Notice: Subject to any disclaimer, the term of this patent is extended or adjusted under 35 U.S.C. 154(b) by 923 days.

(21) Appl. No.: 15/319,232

(22) PCT Filed: Jun. 18, 2014

(86) PCT No.: PCT/SE2014/050752
§ 371 (c)(1),
(2) Date: Dec. 15, 2016

(87) PCT Pub. No.: WO2015/195007
PCT Pub. Date: Dec. 23, 2015

(65) Prior Publication Data
US 2017/0119983 A1    May 4, 2017

(51) Int. Cl.
*A61M 16/00* (2006.01)
*A61M 16/12* (2006.01)
(Continued)

(52) U.S. Cl.
CPC ...... *A61M 16/0051* (2013.01); *A61M 16/024* (2017.08); *A61M 16/0833* (2014.02);
(Continued)

(58) Field of Classification Search
CPC .... A61M 2016/0027; A61M 2016/003; A61M 2016/0033; A61M 2016/0036; A61M 2016/0039; A61M 2016/102; A61M 2205/14; A61M 2205/15; A61M 2205/18; A61M 2205/50; A61M 2205/505; A61M 2205/581; A61M 2205/583;
(Continued)

(56) References Cited

U.S. PATENT DOCUMENTS 5,918,596 A * 7/1999 Heinonen ............. A61M 16/12
128/204.21
6,125,846 A   10/2000 Bathe et al.
(Continued)

FOREIGN PATENT DOCUMENTS

EP     0937479 A2   8/1999
JP     08047534 A   2/1996
(Continued)

*Primary Examiner* — Joseph D. Boecker
(74) *Attorney, Agent, or Firm* — Schiff Hardin LLP

(57) ABSTRACT

An additive gas delivery apparatus, system and method for delivery of additive gas, such as nitric oxide [NO], to a patient use a control computer configured to determine if a monitored parameter indicates that a patient is connected to the additive gas delivery apparatus, determine if the additive gas delivery apparatus is in a passive state in which it does not deliver additive gas, and activate an alarm if the additive gas delivery apparatus is in said passive state when the monitored parameter indicates that a patient is connected to the additive gas deliver apparatus. The alarm serves to notify the user of undesired non-delivery of additive gas, and so serves to improve safety in additive gas delivery systems.

15 Claims, 2 Drawing Sheets

(51) Int. Cl.
  *A61M 16/16* (2006.01)
  *A61M 16/08* (2006.01)
  *A61M 16/10* (2006.01)

(52) U.S. Cl.
  CPC .......... *A61M 16/12* (2013.01); *A61M 16/16* (2013.01); *A61M 16/085* (2014.02); *A61M 2016/003* (2013.01); *A61M 2016/0021* (2013.01); *A61M 2016/0027* (2013.01); *A61M 2016/0036* (2013.01); *A61M 2016/0039* (2013.01); *A61M 2016/102* (2013.01); *A61M 2202/0275* (2013.01); *A61M 2205/13* (2013.01); *A61M 2205/18* (2013.01); *A61M 2205/3331* (2013.01); *A61M 2205/3569* (2013.01); *A61M 2205/3592* (2013.01); *A61M 2205/505* (2013.01); *A61M 2205/581* (2013.01); *A61M 2205/582* (2013.01); *A61M 2205/583* (2013.01)

(58) Field of Classification Search
  CPC .......... A61M 2205/6027; A61M 16/00; A61M 16/0003; A61M 16/0051; A61M 16/0057; A61M 16/01; A61M 16/022; A61M 16/024; A61M 16/0816; A61M 16/0833; A61M 16/085; A61M 16/0875; A61M 16/0883; A61M 16/12; A61M 16/16
  See application file for complete search history.

(56) References Cited

U.S. PATENT DOCUMENTS

| | | | |
|---|---|---|---|
| 6,851,427 B1 * | 2/2005 | Nashed | A61M 16/021 128/205.23 |
| 6,962,154 B2 | 11/2005 | Krebs | |
| 2003/0135087 A1 | 7/2003 | Hickle et al. | |
| 2010/0071689 A1 * | 3/2010 | Thiessen | A61M 16/0051 128/202.22 |
| 2012/0031402 A1 | 2/2012 | Loncar et al. | |
| 2013/0074838 A1 * | 3/2013 | Bathe | A61M 16/104 128/203.12 |
| 2013/0125883 A1 * | 5/2013 | Bonassa | A61M 16/0057 128/202.22 |

FOREIGN PATENT DOCUMENTS

| | | |
|---|---|---|
| JP | 2000300674 A | 10/2000 |
| WO | WO-2008/148134 A1 | 12/2008 |

* cited by examiner

ADDITIVE GAS DELIVERY APPARATUS

BACKGROUND OF THE INVENTION

Field of the Invention

The present invention relates to an additive gas delivery apparatus for delivery of additive gas to a patient. In particular, the invention relates to a nitric oxide (NO) delivery apparatus for delivery of NO to a patient in need of NO therapy. The invention also relates to a gas delivery system and a method for monitoring delivery of additive gas to a patient.

Description of the Prior Art

In conjunction with respiratory care of a patient provided by means of a breathing apparatus, such as a ventilator, respirator or Anaesthesia machine, the physician may sometimes wish to supplement the breathing gas with an additive gas having a desired medical effect on the patient. Nitric oxide (NO), also known as nitrogen monoxide, is an example of such an additive gas.

In small quantities, NO can have several beneficial effects on the pulmonary function of a subject. In particular, NO has a vasodilating effect and prompt supply of NO may be life critical to patients suffering from vascular spasms in the pulmonary capillaries.

In existing NO delivery systems it is normally up to the operator to ensure that NO is delivered to the patient connected to the NO delivery system by correctly interpreting state feedback provided to the operator via a user interface of the treatment device or a monitoring system monitoring the treatment currently being provided to the patient. This setup is sensitive to mistakes and misunderstandings, sometimes leading to situations where activation of NO therapy is forgotten or where NO therapy is accidentally interrupted.

This risk is particularly prominent for system setups where a standalone NO delivery apparatus is connected to a ventilator circuit to deliver a flow of NO into a flow of breathing gas that is to be supplied to a ventilated patient. Since the NO delivery apparatus typically has to be activated manually and independently of the ventilator in order to start delivering NO, there is a risk that the system operator, after having activated and configured the ventilator, forgets to activate the NO delivery apparatus.

Although critical to patient safety, this problem is not addressed by known NO delivery systems according to prior art. Instead, NO delivery systems according to prior art rather focus on the problem of how to avoid formation and delivery of highly toxic nitrogen dioxide, $NO_2$, to the patient, which is a delicate problem since NO is converted into $NO_2$ over the course of time when in contact with oxygen containing gas, such as air.

For example, EP937479 discloses an NO delivery system including certain functions to provide protection against the inadvertent formation of $NO_2$ through the reaction of NO and $O_2$ within the device itself. This is partly achieved by functionality for detecting attempts to inhale by the patient and, if attempts to inhale cannot be detected for a certain period of time, e.g. 15 seconds, the system will automatically deliver a pulse of NO so that the device purges itself and rids the possible formation of any $NO_2$ that may have formed since the last pulse of NO was administered. Another feature of the proposed NO delivery system is the activation of an alarm to alert the user of a situation in which no attempts to inhale has been made by the patient during a predetermined period of time, alerting the user to the situation to take prompt action to determine the problem.

U.S. Pat. No. 6,962,154 also discloses an NO delivery system, which system includes functionality for purging itself with one or more other gases to avoid delivery of $NO_2$ to the patient.

U.S. Pat. No. 6,125,846 is yet another document describing an NO delivery system equipped with purging functionality to avoid administration of $NO_2$ to a patient. Here, to avoid formation and administration of $NO_2$ after interruption in NO administration, the system comprises means for sensing the commencement of an active state in which the system is capable of delivering NO containing gas to a patient, and for purging the system with NO containing gas during a predetermined period of time when the commencement of an active state is sensed.

Thus, there are several disclosures of NO delivery systems addressing the problem of how to mitigate the risk of formation and unintentional administration of $NO_2$. However, there are no known NO delivery systems addressing the problem of how to minimize the risk of unintentional non-delivery of NO to patients in NO delivery systems.

As mentioned above, unintentional non-delivery of NO to a patient in need of NO therapy is a life-threatening situation. To avoid such situations there is thus a need for a safer and more user-friendly NO delivery system.

SUMMARY OF THE INVENTION

It is an object of the present invention to provide a safe and user-friendly additive gas delivery apparatus for delivery of additive gas, such as NO, to a patient.

It is a particular object of the invention to minimize the risk of unintentional non-delivery of NO to patients in need of NO therapy.

This and other objects which will be apparent from the detailed description following hereinafter are achieved by means of an additive gas delivery apparatus for delivery of additive gas, such as NO, to a patient. The additive gas delivery apparatus has a control computer configured to determine if a monitored parameter indicates that a patient is connected to the additive gas delivery apparatus. The control computer is further configured to determine if the additive gas delivery apparatus is in a passive state in which it does not deliver additive gas, and to activate an alarm if the gas delivery apparatus is in said passive state when said monitored parameter indicates that a patient is connected thereto.

This has the effect of notifying the system operator about situations in which a patient is connected to the additive gas delivery apparatus without receiving any additive gas, i.e. of situations in which a patient is not treated although connected to the additive gas delivery apparatus. Thereby, the invention has the effect of preventing undesired non-delivery of additive gas, such as NO, to patients in urgent need of NO therapy.

In particular, the invention serves to avoid situations in which the operator of an NO delivery apparatus starts up the apparatus to put it in a standby operational mode in which it is ready for NO delivery, and then forgets to switch from the standby mode to an active operational mode in which NO delivery is activated when the need for NO therapy arises.

That a patient is or at least can be assumed to be connected to the additive gas delivery apparatus based on the at least one monitored parameter, and that the apparatus is in a passive state in which it does not deliver additive gas, are hence two conditions, hereinafter referred to as alarm conditions, which have to be fulfilled in order for the control computer of the apparatus to activate the alarm. The control computer is hence configured to check whether the alarm conditions are fulfilled based on at least one parameter indicative of the presence of a patient connected to the additive gas delivery apparatus, and at least one parameter indicative of the current state of the apparatus.

The at least one parameter used by the control computer in the determination as to whether a patient is or can be assumed to be connected to the additive gas delivery apparatus will hereinafter be referred to as a patient indicator.

In a preferred embodiment, the patient indicator is a parameter relating to a flow and/or pressure, typically a flow and/or pressure indicative of breathing activity of a patient. Said breathing activity may be spontaneous breathing activity caused by the patient itself or supported or controlled breathing activity partially or fully caused by a breathing apparatus, such as a ventilator, to which the patient is connected to receive ventilatory support.

Thus, the control computer of the additive gas delivery apparatus may be configured to detect connection of a patient to the additive gas delivery apparatus based on changes in a monitored flow and/or pressure, which changes may be caused by spontaneous breathing of a patient and/or by the supply of breathing gas to a patient provided by a breathing apparatus to which the patient is connected.

The control computer of the additive gas delivery apparatus is preferably configured to determine whether the apparatus is in said passive state by determining a current operational mode of the additive gas delivery apparatus, i.e. a mode of operation in which the additive gas delivery apparatus is currently being operated.

The additive gas delivery apparatus of the invention is preferably configured to be operated in one of a plurality of different operational modes, at least one of which is an active operational mode in which additive gas is delivered by the apparatus, and one of which is a passive operational mode in which additive gas is not delivered by the apparatus. In an exemplary embodiment of the invention, the additive gas delivery apparatus is configured to be operated in any of a plurality of operational modes comprising at least an active operational mode herein referred to as "running mode", and a passive operational mode herein referred to as "standby mode".

The additive gas delivery apparatus is in a passive state when operated in a passive operational mode and in an active state when operated in an active operational mode. By determining the current operational mode of the additive gas delivery apparatus, the control computer can hence determine whether the apparatus is in an active or passive state and so whether or not additive gas is currently being delivered by the apparatus.

The current operational mode and thus the current state of the additive gas delivery apparatus is typically determined by the control computer based on the value of a software parameter indicative of the current operational mode of the gas delivery apparatus. In order for the software parameter to accurately reflect the current operational mode of the apparatus, the value of the parameter is typically updated by the control computer each time there is a change in operational mode of the additive gas delivery apparatus. The control computer of the additive gas delivery apparatus may hence be configured to keep track of the current state of the additive gas delivery apparatus by use of said software parameter.

A change in operational mode of the additive gas delivery apparatus is typically initiated by an operator of the apparatus through user input on a user interface of the apparatus. Upon reception of user input indicating a desired change in operational mode of the additive gas delivery apparatus, the control computer effectuates said change by changing one or more operational parameters of the additive gas delivery apparatus. When the operational mode has been changed to a new operational mode, the control computer changes the value of the software parameter to a value reflecting said new operational mode.

From the above it is clear that, according to one aspect of the invention, the additive gas delivery apparatus comprises a control computer that is configured to:
  determine if a monitored parameter serving as a patient indicator indicates that a patient is connected to the additive gas delivery apparatus, wherein said monitored parameter relates to a flow and/or pressure indicative of spontaneous, supported or controlled breathing activity of the patient;
  determine if the additive gas delivery apparatus is in a passive state in which it does not deliver additive gas, based on a current operational mode of the gas delivery apparatus, and
  activate an alarm if the additive gas delivery apparatus is in a passive state when said monitored parameter indicates that a patient is connected thereto.

Thus, the control computer may be configured to determine if the patient indicator indicates that a patient is connected to the additive gas delivery apparatus, determine the operational mode of the additive gas delivery apparatus, and activate an alarm if the apparatus is operated in a passive operational mode when the patient indicator indicates that a patient is connected thereto.

In one embodiment, the control computer is configured to generate the alarm only if it can determine, through monitoring of the patient indicator, that a patient has been connected to the additive gas delivery apparatus at least for a predetermined period of time, hereinafter referred to as the alarm delay time, during which the apparatus has been in a passive state. This has the effect of preventing the alarm from being activated immediately when the patient is connected to the additive gas delivery apparatus, and so gives the operator at least some time to put the apparatus in an active state before the alarm is generated. The alarm delay time may be pre-set to a fixed value, e.g. 60 seconds, or adjustable by the apparatus operator.

The alarm may be any type of visual, audible and/or vibratory alarm serving to attract the attention of the operator of the additive gas delivery apparatus.

Preferably, the control computer is further configured to deactivate the alarm in response to reception of user input indicating that an operator of the apparatus has noticed the alarm, which user input hence constitutes a deactivation command serving to deactivate the alarm. In one embodiment, the control computer is configured to activate the alarm by causing display of a visual alarm, e.g. in form of a certain symbol or combination of symbols, on a touchscreen of the additive gas delivery apparatus. In this embodiment, the deactivation command may be input by the operator on the same touchscreen.

As discussed above, the control computer is preferably configured to determine whether or not a patient seems to be connected to the apparatus based on a monitored flow and/or pressure indicative of breathing activity of a patient. To this end, flow and/or pressure measurements may be obtained by means of at least one flow and/or pressure sensor, configured to measure a flow and/or pressure indicative of breathing activity of the patient in a breathing circuit to which the patient is connected.

For example, the additive gas delivery apparatus may have a flow and/or pressure sensor configured to be detachably connected to an inspiratory line of a breathing apparatus circuit to which the patient is connected, and configured to measure a flow and/or pressure indicative of spontaneous, supported or controlled breathing activity of the patient in said inspiratory line, which flow and/or pressure may be used as a patient indicator indicative of connection of a patient to the additive gas delivery apparatus as described above.

Instead or in addition to a patient indicator relating to flow and/or pressure measurements obtained by a flow and/or pressure sensor of the additive gas delivery apparatus, connection of a patient to the additive gas delivery apparatus may be established by the control computer based on a patient indicator relating to a flow and/or pressure measured by a flow and/or pressure sensor of a breathing apparatus to which the additive gas delivery apparatus is communicatively connected. In one embodiment, the additive gas delivery apparatus is communicatively connected to a breathing apparatus to which the patient is connected, and configured to receive from said breathing apparatus information related to flow and/or pressure measurements indicative of spontaneous, supported or controlled breathing activity of the patient, obtained by one or more flow and/or pressure sensors of the breathing apparatus.

It should be appreciated that "additive gas" herein refers to any medical gas that is added to a breathing gas or carrier gas for subsequent delivery to a patient, which medical gas has a therapeutic effect on said patient. The additive gas may for example be nitric oxide, anesthetics, analgesics, carbon oxide or xenon.

In a preferred embodiment, the additive gas is NO and the additive gas delivery apparatus is an NO delivery apparatus. The NO delivery apparatus is configured to add NO to a breathing gas to form an NO containing breathing gas mixture to be supplied to the patient.

Commercially available NO supplies are provided in form of pressurized gas cylinders containing a predetermined mixture of NO and a carrier gas, such as nitrogen. When in this document talking about delivering, adding, supplying, administrating or dosing NO it should thus be appreciated that this typically means delivering, adding, supplying, administrating or dosing an NO containing carrier gas, typically in form of NO containing nitrogen.

Preferably, the additive gas delivery apparatus of the invention is a standalone single-unit apparatus, meaning that it is a separate and self-contained unit. Even more preferably, the additive gas delivery apparatus is a standalone apparatus that is configured to be detachably connected to a breathing apparatus circuit for adding the additive gas to a flow of breathing gas provided to a patient by a breathing apparatus, i.e. for dosing additive gas into a flow of breathing gas that is to be provided to a patient undergoing ventilatory treatment.

In a preferred embodiment, the additive gas delivery apparatus of the invention is a standalone additive gas delivery apparatus that is detachably connectable to an inspiratory line of a breathing apparatus circuit having a breathing apparatus, such as a ventilator, respirator or Anaesthesia machine, which breathing apparatus is connected to the patient for supplying breathing gas to the patient via said inspiratory line. The additive gas delivery apparatus is configured to add the additive gas to the breathing gas within said inspiratory line to form an additive gas containing breathing gas mixture for subsequent delivery to the airways of the patient.

In other embodiments, the additive gas delivery apparatus may have an internal gas mixing unit for mixing additive gas, such as NO, with breathing gas, such as $O_2$ or air, to form an additive gas containing breathing gas mixture for direct delivery to the patient, e.g. via a gas conduit directly connecting the additive gas delivery apparatus to the airways of the patient via a breathing mask or a nasal cannula. Thus, in this embodiment, the additive gas delivery apparatus is configured not to deliver the additive gas to the patient via a breathing apparatus circuit to which the additive gas delivery apparatus is connectable. Instead, the additive gas is delivered to the patient via a direct connection between the additive gas delivery apparatus and the patient, through which no other gases than the additive gas containing breathing gas mixture from the additive gas delivery apparatus is delivered to the patient.

According to another aspect of the invention, there is provided a method for monitoring delivery of additive gas to a patient by an additive gas delivery apparatus. The method includes the steps of:

determining if at least one monitored parameter indicates that a patient is connected to the additive gas delivery apparatus;

determining if the additive gas delivery apparatus is in a passive state in which it does not deliver additive gas, and activating an alarm if the additive gas delivery apparatus is in said passive state when a patient is connected thereto.

As discussed above, the determination as to whether or not a patient is connected to the additive gas delivery apparatus is typically based on a patient indicator relating to a flow and/or pressure indicative of spontaneous, supported or controlled breathing activity of the patient, whereas determination of the state of the additive gas delivery apparatus typically involves determination of the current operational mode of the apparatus, which in turn may be determined based on a software parameter that is used by the control computer to keep track of the current operational mode of the additive gas delivery apparatus.

More advantageous aspects and effects of the method as well as the gas delivery system and the additive gas delivery apparatus of the invention will be described in the detailed description following hereinafter.

DESCRIPTION OF THE PREFERRED EMBODIMENTS

The present invention relates to an additive gas delivery apparatus for delivery of an additive gas to a patient.

Figure 1:
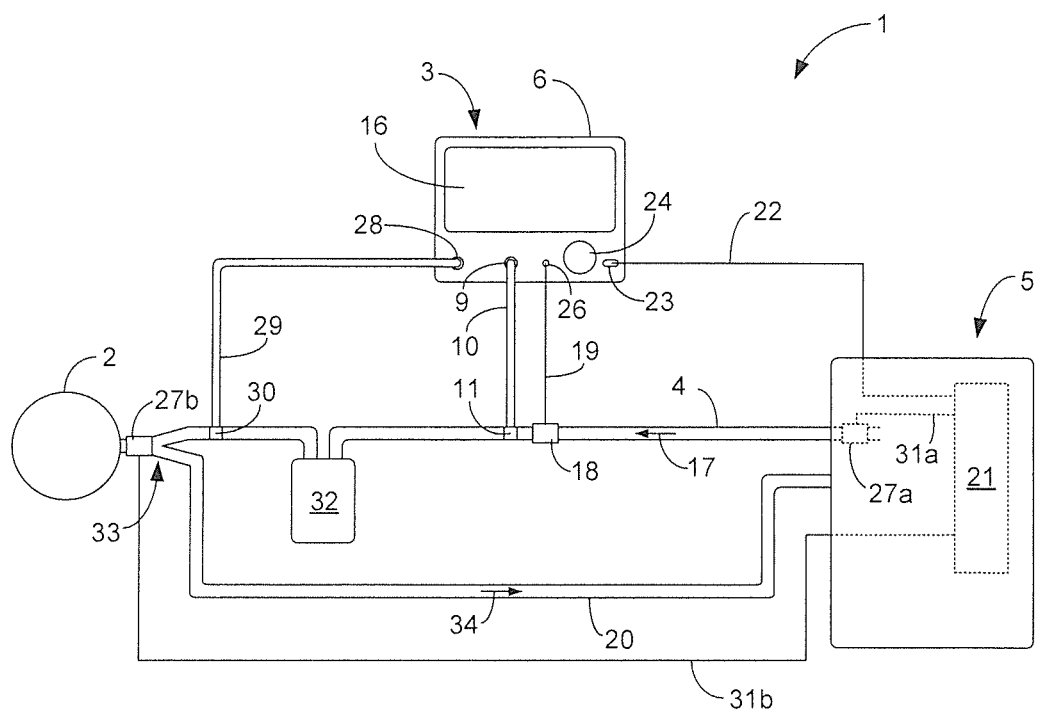
FIG. 1 illustrates schematically a gas delivery system comprising an additive gas delivery apparatus according to an exemplary embodiment of the invention.

FIG. 1 illustrates a gas delivery system 1 for providing a mixture of breathing gas and additive gas to a patient 2. The gas delivery system 1 comprises an additive gas delivery apparatus 3 according to an exemplary embodiment of the present invention.

The additive gas delivery apparatus 3 is detachably connected to an inspiratory line 4 of a breathing apparatus circuit to which the patient 2 is connected. The breathing apparatus circuit comprises a breathing apparatus 5, e.g. in form of a ventilator, which breathing apparatus 5 is arranged to provide ventilatory support to the patient 2 through the supply of breathing gas to the patient 2 via said inspiratory line 4. The breathing gas is typically oxygen ($O_2$), air or a mixture therebetween but may be any oxygen-containing gas mixture suitable for respiration. A humidifier 32 is arranged in the inspiratory line 4 for humidifying a breathing gas mixture before being delivered to the airways of the patient 2. The breathing apparatus circuit further comprises a Y-piece 33 connecting the inspiratory line 4 and the patient 2 to an expiratory line 20 conveying expiration gases away from the patient 2, as indicated by the arrow 34 in the expiratory line 20.

In a preferred embodiment, the additive gas delivered to the patient 2 by the additive gas delivery apparatus 3 is nitric oxide, NO, and, therefore, the additive gas delivery apparatus 3 will hereinafter be referred to as an NO delivery apparatus. In other embodiments not further described in this document, the additive gas delivery apparatus 3 may be configured for delivery of another additive gas having a therapeutic effect on the patient 2, e.g. an anesthetic gas, an analgesic gas, inhalation agents, inhalation medication, carbon oxide or xenon.

Figure 2:
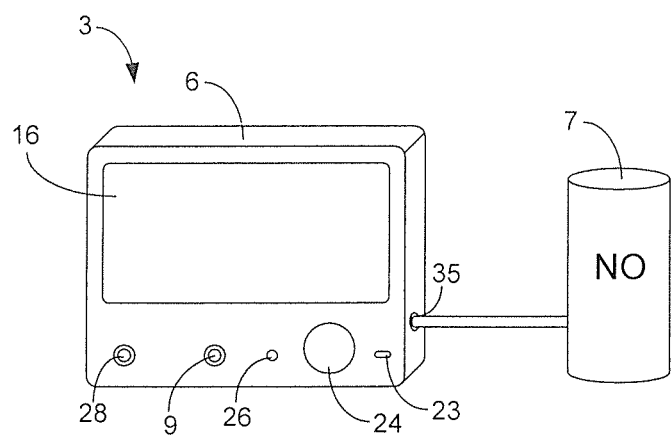
FIG. 2 illustrates schematically certain parts and components of the additive gas delivery apparatus of FIG. 1, and an external source of additive gas to which the additive gas delivery apparatus is connected.
Figure 3:
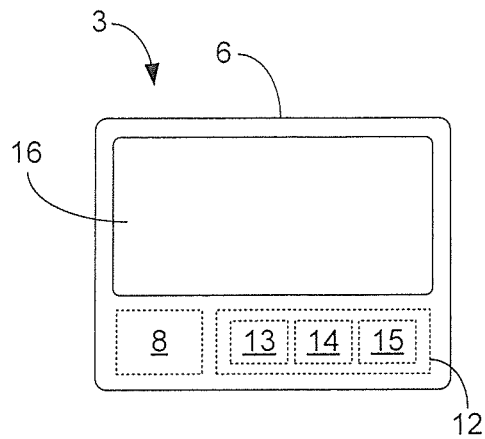
FIG. 3 illustrates schematically internal components of the additive gas delivery apparatus in FIGS. 1-2.

With simultaneous reference now made to FIGS. 1-3, the NO delivery apparatus 3 is a standalone, single unit comprising a housing 6 which encapsulates the internal components of the NO delivery apparatus 3. The housing 6 has a first gas inlet 35 through which the apparatus 3 is connectable to an external NO supply 7 in form of a pressurized NO gas cylinder. The NO cylinder typically contains a gas mixture consisting of NO and a carrier gas in form of nitrogen, which gas mixture may have an NO concentration of e.g. 450, 800 or 900 ppm. Hereinafter, this gas mixture will simply be referred to as NO.

The NO delivery apparatus 3 further has an internal gas processing module 8. Said gas processing module 8 has a gas regulator (not shown) for adapting the flow of pressurized NO received from the NO supply 7 to a suitable flow profile according to which NO is delivered by the NO delivery apparatus 3 via a gas outlet 9 of the housing 6 and further via a gas delivery conduit 10 into the inspiratory line 4 of the breathing apparatus circuit for further delivery to the patient 2. The gas regulator of the gas processing module 8 is typically configured to control the flow of NO delivered into the inspiratory line 4 of the breathing apparatus circuit to obtain a user-selectable, constant concentration of NO in the breathing gas mixture delivered to the patient, typically within the range of 0-80 ppm and normally within the range of 0-20 ppm. To this end, the gas regulator may be configured to control the delivered flow of NO based on NO concentration measurements obtained downstream the point of delivery of NO in the inspiratory line 4. Flow measurements obtained in the inspiratory line 4 may also be used by said gas regulator to control the delivered flow of NO to ensure a substantially constant concentration of NO in the breathing gas mixture delivered to the patient 2, even in different phases of the respiratory cycle and with varying breathing apparatus settings and modes.

In this embodiment, the gas delivery conduit 10 is detachably connected to the inspiratory line 4 of the breathing apparatus circuit by a conduit connector 11 constituting said point of delivery of NO into the inspiratory line 4. Thus, the standalone, single unit NO delivery apparatus 3 is detachably connected to an inspiratory line 4 of a breathing apparatus circuit and configured to deliver a flow of NO into a flow of breathing gas in said inspiratory line 4, which flow of breathing gas is provided by a breathing apparatus 5 connected to one end of said inspiratory line 4, for subsequent delivery of an NO containing breathing gas mixture to a patient 2, connected to the other end of said inspiratory line 4.

As discussed in the background portion, prompt supply of NO may be life critical e.g. to patients suffering from vascular spasms in the pulmonary capillaries and, therefore, it is of utmost importance that NO therapy is activated without further delay when a patient in need of such therapy is connected to the breathing apparatus circuit.

When a patient is to receive NO therapy, the system operator typically starts-up the NO delivery apparatus 3 by pressing a power switch. The NO delivery apparatus 3 is then configured to enter into an operational mode, herein referred to as the pre-use mode, in which a pre-use check is performed. In the pre-use mode, the NO delivery apparatus 3 carries out a plurality of steps being part of said pre-use check in order to put the NO delivery apparatus 3 in another operational mode, herein referred to as the standby mode, in which it is ready to start delivering NO to the patient 2. One important step of this pre-use check is to purge the system from highly toxic nitrogen dioxide, $NO_2$, to prevent delivery thereof to the patient 2 once NO delivery is initiated. When the pre-use check is finished, the NO delivery apparatus 3 may be configured to display information related to the result of the pre-use check on a display, e.g. on a touchscreen 16 of the apparatus 3, and to enter into the standby mode either automatically upon completion of the pre-use check or upon reception of user input instructing the apparatus to switch from pre-use mode to standby mode. When operated in standby mode, the NO delivery apparatus is in a passive state, meaning that it is not operable to deliver NO to a patient.

When the NO delivery apparatus 3 has entered into standby mode, and when the patient 2 is properly connected to the breathing apparatus circuit and the breathing apparatus 5 is activated and configured for the desired ventilatory treatment, the system operator has to remember to put the NO delivery apparatus 3 in an active state to start the NO treatment. This is typically achieved by instructing the NO delivery apparatus to enter into another operational mode, herein referred to as running mode, in which it delivers NO through the gas outlet 9. Putting the NO delivery apparatus 3 into running mode may, according to one embodiment, be achieved by pressing a button of the NO delivery apparatus 3, e.g. a touch-button labelled "start treatment" displayed on said touchscreen 16.

To avoid a situation in which the system operator forgets to start NO therapy, the NO delivery apparatus 3 of the invention is provided with functionality for determining if one or more monitored parameters indicate that a patient 2 is connected to the NO delivery apparatus 3, and for determining if the apparatus 3 is in a passive state in which it does not deliver NO. If said determinations indicate that a patient is connected to the apparatus 3 and that the apparatus in spite of a patient being connected thereto is run in a passive state in which NO therapy is inactivated, an alarm is activated by the apparatus.

As illustrated in FIG. 3, the NO delivery apparatus 3 has an internal control computer 12. The control computer 12 is typically realized in form of at least one data processor (not shown) configured to execute computer program code stored in form of at least one computer program in at least one non-volatile memory (not shown) of the NO delivery apparatus 3. Unless stated otherwise, functions herein described as being performed by the control computer 12 are performed by the processor through execution of the computer program stored in the non-volatile memory of the NO delivery apparatus 3.

The control computer 12 has three functional modules 13, 14, 15 typically realized in form of software modules comprising program code for providing different functionalities of the control computer 12.

The first functional module of the control computer 12 is a patient indicator module 13. The patient indicator module 13 is configured to determine if a patient is connected to the NO delivery apparatus 3, i.e. if the NO gas outlet 9 of the housing 6 is in gaseous communication with the airways of a patient 2. That the patient indicator module 13 is configured to determine if a patient is connected to the NO delivery apparatus 3 means that it is configured to determine if a parameter, typically related to a sensed flow and/or pressure, indicates that a patient is connected to the apparatus 3. A parameter used by the patient indicator module 13 in the determination as to whether a patient is connected to the NO delivery apparatus 3 is hereinafter referred to as a patient indicator.

As mentioned above, the patient indicator is typically a parameter relating to a flow and/or pressure, and typically a flow and/or pressure indicative of breathing activity of the patient 2. Said breathing activity may be spontaneous breathing activity caused by the patient 2 itself, or it may be supported or controlled breathing activity partially or fully caused by the breathing apparatus 5 to which the patient is connected to receive ventilatory support. The arrow 17 indicates a flow of breathing gas in the inspiratory line 4 of the breathing apparatus circuit, which flow according to a preferred embodiment of the invention may be used as patient indicator by the patient indicator module 13 in the determination as to whether the patient 2 is connected to the gas delivery apparatus 3. Said flow may be generated either by a spontaneous inhalation of the patient 2, or by a supported or controlled inhalation of the patient 2 through the supply of pressurized breathing gas into the inspiratory line 4 by the breathing apparatus 5.

To monitor the aforementioned flow, the NO delivery apparatus 3 has a flow sensor 18. The flow sensor 18 is an external flow sensor of the NO delivery apparatus 3, meaning that it is located outside the apparatus housing 6, which flow sensor 18 is configured to be detachably connected to the inspiratory line 4 of the breathing apparatus circuit to monitor the flow therein. Information related to the flow measurements obtained by the flow sensor 18 is sent to the patient indicator unit 13 via a wired or wireless signaling link 19. This information is then received by the patient indicator unit 13 on a sensor communication port 26 of the NO delivery apparatus 3, and used as patient indicator to determine whether or not a patient 2 is connected to the NO delivery apparatus 3.

Instead or in addition to the external flow sensor 18 of the NO delivery apparatus 3, the NO delivery apparatus 3 may be equipped with a communication unit (not shown) configured to communicate with the breathing apparatus 5 and to receive therefrom information related to a flow and/or pressure indicative of breathing activity of the patient 2, which flow and/or pressure is measured by means of a flow and/or pressure sensor of said breathing apparatus 5. For example, the breathing apparatus 5 may be equipped with a flow and/or pressure sensor 27a arranged in an inspiratory part of the breathing apparatus 5 and/or a flow and/or pressure sensor 27b arranged in the Y-piece 33 connecting the inspiratory line 4 and the expiratory line 20 of the breathing apparatus circuit with the patient 2. Flow and/or pressure measurements obtained by said sensors 27a, 27b may be communicated to a control computer 21 of the breathing apparatus 5 via sensor links 31a, 31b and forwarded to the patient indicator unit 13 of the NO delivery apparatus 3 for use as patient indicator in the determination of a connection to the patient 2. The information related to the flow and/or pressure measurements may be communicated from the breathing apparatus 5 to the NO delivery apparatus 3 via a wired or wireless communication link 22. In one exemplary embodiment, the NO delivery apparatus is provided with a RS-232 interface 23, and the communication link 22 is an RS-232 communication link.

Thus, the patient indicator module 13 is configured to monitor at least one parameter serving as a patient indicator, and to determine whether the parameter indicates that a patient is connected to the NO delivery apparatus 3. This may be achieved by the patient indicator module 13 by comparing the monitored parameter with a predetermined threshold value, e.g. a threshold value for flow corresponding to a flow which can only be caused by spontaneous, supported or controlled breathing activity of the patient 2, and so indicates the presence of a patient 2 connected to the NO delivery apparatus 3.

The second functional module of the control computer 12 is a state tracking module 14. The state tracking module 14 is configured to determine if the NO delivery apparatus 3 is in a passive state in which it does not deliver NO. To this end, the state tracking module 14 is configured to always keep track of the current state of the NO delivery apparatus 3. The current state of the apparatus 3 is in turn monitored by the state tracking module 14 by monitoring a software parameter provided with a parameter value representing the current operational mode of the NO delivery apparatus. If said software parameter indicates that the NO delivery apparatus is presently operated in standby mode or any other operational mode in which NO delivery is not activated, the state tracking module 14 concludes that the apparatus 3 is in a passive state. Thus, the state tracking module 14 is configured to determine the current state of the NO delivery apparatus based on a software parameter indicative of the current operational mode of the NO delivery apparatus.

In order for the software parameter to accurately reflect the current operational mode of the apparatus, the state tracking module 14 of the control computer 12 is further configured to update the value of the software parameter whenever there is a change in operational mode of the NO delivery apparatus 3.

When there is a change in operational mode of the NO delivery apparatus 3, e.g. an automatic or operator-initiated change from the pre-use mode to the standby mode as discussed above, or an operator-initiated change from the standby mode to the running mode, as also discussed above, the control computer 12 of the NO delivery apparatus 3 is configured to change one or more operational parameters of the NO delivery apparatus in order to put the apparatus 3 in the new operational mode. When said operational parameters have been changed by the control computer 12 and the apparatus 3 is operated in the new operational mode, the state tracking module 14 changes the value of said software parameter to a value indicative of the new operational mode.

Although in the above described embodiment being provided with a parameter value reflecting the current operational mode of the NO delivery apparatus 3, it should be appreciated that it may be sufficient for the software parameter to indicate whether the apparatus 3 is currently operated in an active state or passive state, i.e. whether or not the NO delivery apparatus 3 is currently in a state in which NO is delivered through the gas outlet 9.

Thus, the software parameter may be any parameter capable of assuming at least two values, one of which represents an active state of the NO delivery apparatus and one of which represents a passive state. Preferably, however, the software parameter is capable of assuming more than two states and preferably as many states as there are operational modes of the NO delivery apparatus in order for the software parameter to indicate not only the current state of the NO delivery apparatus 3 but also the specific mode of operation in which the apparatus 3 is currently operated.

The third functional module of the control computer 12 is an alarm activation module 15. The alarm activation module 15 is configured to activate an alarm if the patient indicator indicates that a patient 2 is connected to the NO delivery apparatus and that the NO delivery apparatus 3 is currently in a passive state in which NO is not delivered by the apparatus. Determination of a patient being or assumingly being connected to the NO delivery apparatus 3 and determination of the NO delivery apparatus 3 being in a passive state are thus two conditions, herein referred to as alarm conditions, which both have to be fulfilled in order for the alarm activation module 15 to activate the alarm.

The alarm may be any type of visual, audible and/or vibratory alarm serving to attract the attention of the operator of the NO delivery apparatus 3.

In one exemplary embodiment, the patient indicator module 13 is configured to determine if a patient is connected to the NO delivery apparatus 3 repeatedly, e.g. every tenth second. Each time the determination conducted by the patient indicator module 13 shows that a patient is connected to the apparatus 3, the state tracking module 14 is configured to determine if the NO delivery apparatus in a passive state. If, at this time, the determination conducted by the state tracking module 14 shows that the apparatus 3 is in a passive state, the alarm activation module 15 may be configured to activate the alarm either directly or with a certain delay, as described below.

The alarm activation module 15 is preferably configured to activate the alarm only if the two alarm conditions have been fulfilled during a predetermined period of time, herein referred to as the alarm delay time. The alarm delay time may be pre-set to a fixed value, e.g. 60 seconds, or adjustable by the system operator. To this end, the alarm activation module 15 may, according to an exemplary embodiment, be configured to count the number of loops during which both alarm conditions have been fulfilled, and to activate the alarm only if both alarm conditions have been fulfilled during a certain number of consecutive loops. This means that in the exemplary embodiment described above in which the alarm conditions are checked once every tenth-second, the alarm activation module 15 may be configured to count the number of ten-second loops during which both alarm conditions have been fulfilled, and to activate the alarm when said number exceeds a predetermined number of loops corresponding to a certain delay time.

Thus, in the exemplary embodiment described above, the control computer 12 is configured to check repeatedly whether the alarm should be activated or not. Preferably, the control computer 12 is also configured to check repeatedly whether the alarm, if active, should be deactivated or not. The control computer 12 may be configured to deactivate the alarm if the patient 2 is disconnected from the NO delivery apparatus, i.e. if the patient indicator indicates that the patient is no longer connected to the NO delivery apparatus 3, or if NO delivery is activated, i.e. if the determination of the state of the NO delivery apparatus 3 shows that the state has been changed from a passive state to an active state.

Furthermore, the alarm activation module 15 is preferably configured to deactivate the alarm in response to reception of user input indicating that the system operator has noticed the alarm, which user input hence constitutes a deactivation command serving to deactivate the alarm. In one embodiment, the alarm activation module 15 is configured to activate the alarm by causing display of a visual alarm on the touchscreen 16 of the NO delivery apparatus 3, and to deactivate the alarm in response to user input received from the system operator via the same touchscreen 16.

Figure 4:
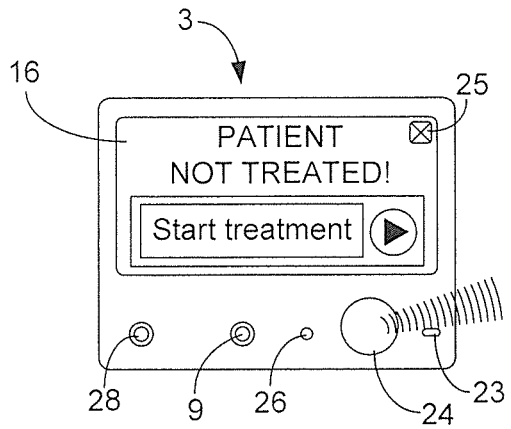
FIG. 4 illustrates schematically an exemplary view of a GUI of the additive gas delivery apparatus in FIGS. 1-3.

This is illustrated in FIG. 4, schematically illustrating an exemplary view of a GUI (graphical user interface) of the NO delivery apparatus 3 when the alarm conditions are fulfilled and the alarm has been activated by the alarm activation module 15 of the control computer 12.

In this exemplary embodiment, activation of the alarm involves display of a visual alarm on the touchscreen 16, and, additionally, generation of an audible alarm produced by means of a speaker 24 of the NO delivery apparatus 3. The display of the visual alarm involves display of a text ("PATIENT NOT TREATED") informing the system operator that the patient 2 is not receiving NO although being connected to the NO delivery apparatus 3. Furthermore, in this exemplary view of the GUI, a touch-button labelled "Start treatment" and a play symbol are displayed together with the visual alarm to remind the system operator to start NO treatment in case forgotten. If the touch-button or the play symbol is pressed, a signal indicating that there is a desire to start NO therapy is sent to the control computer 12, whereupon the control computer 12 puts the NO delivery apparatus 3 in running mode and activates NO delivery. Also, this exemplary view of the GUI comprises a symbol 25, here in form of an X-button, by means of which the system operator can deactivate the alarm although the alarm conditions are still fulfilled. By pressing the X-button, the system operator indicates to the control computer 12 of the NO delivery apparatus 3 that the alarm has been noticed and that NO therapy is not currently desired. Upon reception of a signal indicating that the X-button has been pressed, the alarm activation module 15 of the control computer 12 deactivates the alarm.

With reference now made to FIGS. 1 and 3, the gas processing module 8 of the NO delivery apparatus 3 further comprises a gas analyzer (not shown). This gas analyzer is configured to receive a sample of a gas mixture via a gas sample port 28 of the NO delivery apparatus 3, and to determine the NO, $NO_2$ and $O_2$ concentrations in said gas sample. The gas sample port 28 is connected to the inspiratory line 4 of the breathing apparatus circuit, downstream the point of delivery of NO from the NO delivery apparatus 3, via a gas sampling conduit 29 detachably connected to the inspiratory line 4 by means of a conduit connector 30. The gas processing module 8 of the NO delivery apparatus 3 further includes a flow generator (not shown) configured to generate a flow of gas from the inspiratory line 4 to the gas analyzer of the gas processing module 8, via said gas sampling conduit 29 and gas sample port 28. The NO, $NO_2$ and $O_2$ concentrations in the gas sample is communicated by the gas analyzer to the control computer 12 of the NO delivery apparatus 3, whereby the control computer 12 may be configured to take actions based on said concentrations, which actions for example may include display of information related to said concentrations on the touchscreen 16, and activation of an alarm in case of too high or too low NO concentration, too high $NO_2$ concentration or too low $O_2$ concentration. Together with the proposed principle of generating an alarm in case the NO delivery apparatus 3 is operated in standby mode or another passive state when a patient 2 is connected thereto, the feature of generating an alarm in case of too low NO concentration downstream the point of delivery of NO in the inspiratory line 4 provides an extra layer of safety allowing the system operator to be alerted also in situations in which no or too low flows of NO is delivered by the NO delivery apparatus 3 when operated in running mode or another active state.

Figure 5:
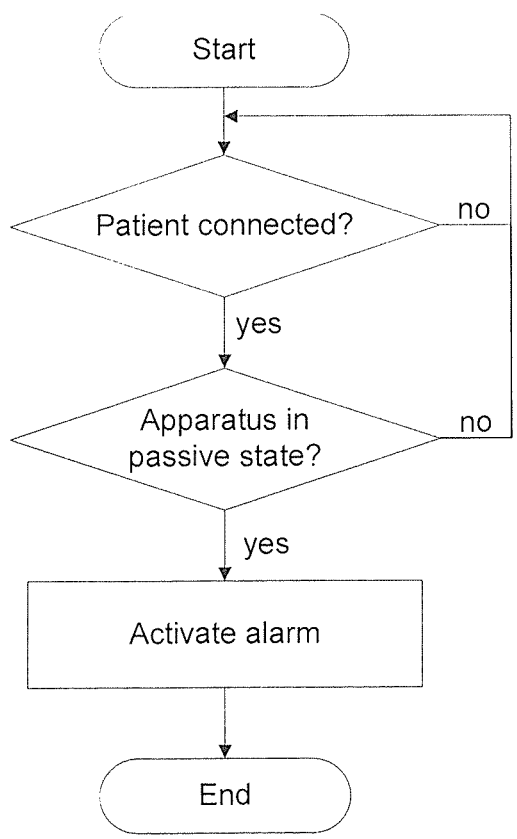
FIG. 5 is a flowchart illustrating a method according to an exemplary embodiment of the invention.

With reference simultaneously made to previous drawings, FIG. 5 illustrates a method for monitoring delivery of NO to the patient 2 by the NO delivery apparatus 3, according to an exemplary embodiment of the present invention. The method is performed by the control computer 12 of the NO delivery apparatus 3, typically through execution of the above mentioned computer program stored in a non-volatile memory of the apparatus 3.

In a first step, S1, determination is made as to whether a patient 2 is or at least seems to be connected to the NO delivery apparatus 3. As described in more detail above, this determination is typically made based on a patient indicator related to a flow and/or pressure indicative of breathing activity of the patient 2. If the determination indicates that a patient is connected to the apparatus 3 the method proceeds to a second step S2. If the determination indicates that no patient is currently connected to the apparatus 3, the method restarts by repeating step S1.

In the second step, S2, determination is made as to whether the NO delivery apparatus 3 is in a passive state in which it does not deliver NO. As described in more detail above, determination of the state of the apparatus is typically made by determining the current operational mode of the apparatus 3, which in turn is determined based on a software parameter having a value that represents the current operational mode of the apparatus 3. If the determination shows that the NO delivery apparatus 3 is in a passive state the method proceeds to a third step S3. If the determination shows that the NO delivery apparatus 3 is in a passive state the method proceeds to a third step S3. If the determination shows that the apparatus is not in a passive state, meaning that it has to be in an active state in which it delivers NO, the method restarts by repeating step S1.

In the third step, S3, a visual, audible and/or vibratory alarm is activated. Consequently, the alarm is activated if: A) a patient is or is assumed to be connected to the NO delivery apparatus, and B) the NO delivery apparatus is in a passive state. As described in more detail above, the alarm is preferably activated only if the alarm conditions A) and B) have been fulfilled during a predetermined period of time constituting what is herein referred to as the alarm delay time.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. An additive gas delivery apparatus for delivery of additive gas to a patient, said additive gas delivery apparatus comprising a control computer configured to:
   determine if a monitored parameter indicates that the patient is connected to the additive gas delivery apparatus;
   determine if the additive gas delivery apparatus is in a passive state in which it does not deliver additive gas, and
   activate an alarm if the additive gas delivery apparatus is in said passive state when said monitored parameter indicates that the patient is connected to the additive gas delivery apparatus.

2. The additive gas delivery apparatus according to claim 1, wherein the control computer is configured to determine whether the additive gas delivery apparatus is in said passive state by determining a current operational mode of the additive gas delivery apparatus.

3. The additive gas delivery apparatus according to claim 2, wherein said control computer is configured to determine the current operational mode of the additive gas delivery apparatus based on a software parameter that is used by the control computer to keep track of the current operational mode of the additive gas delivery apparatus.

4. The additive gas delivery apparatus according to claim 1, wherein said monitored parameter relates to a flow and/or pressure indicative of spontaneous, supported or controlled breathing activity of the patient.

5. The additive gas delivery apparatus according to claim 1, wherein the additive gas delivery apparatus is configured to add the additive gas to a breathing gas to form an additive gas containing breathing gas mixture to be supplied to the patient.

6. The additive gas delivery apparatus according to claim 1, wherein said additive gas delivery apparatus is configured to be detachably connected to an inspiratory line of a breathing apparatus circuit comprising a breathing apparatus for supplying breathing gas to said patient via said inspiratory line, and configured to deliver additive gas into the breathing gas within said inspiratory line for subsequent delivery of an additive gas containing breathing gas mixture to said patient.

7. The additive gas delivery apparatus according to claim 6, wherein said additive gas delivery apparatus further comprises a flow and/or pressure sensor configured to be detachably connected to said inspiratory line of said breathing apparatus circuit for measuring a flow and/or pressure indicative of spontaneous, supported or controlled breathing activity of the patient.

8. The additive gas delivery apparatus according to claim 6, wherein said additive gas delivery apparatus is configured to be communicatively connected to said breathing apparatus and to receive information related to said flow and/or pressure indicative of spontaneous, supported or controlled breathing activity of the patient from the breathing apparatus, said flow and/or pressure being measured by a flow and/or pressure sensor of the breathing apparatus.

9. The additive gas delivery apparatus according to claim 1, wherein the additive gas is nitric oxide (NO) and the additive gas delivery apparatus is an NO delivery apparatus.

10. A gas delivery system comprising:
    a breathing apparatus connectable to a patient via a breathing apparatus circuit and configured to provide breathing gas to said patient via an inspiratory line of said breathing apparatus circuit;

an additive gas delivery apparatus configured to be detachably connected to said inspiratory line and to deliver additive gas into the breathing gas within said inspiratory line for subsequent delivery of an additive gas containing breathing gas mixture to said patient; and a computer configured to determine if a monitored parameter indicates that the patient is connected to the additive gas delivery apparatus, determine if the additive gas delivery apparatus is in a passive state in which it does not deliver additive gas, and activate an alarm if the additive gas delivery apparatus is in said passive state when said monitored parameter indicates that the patient is connected to the additive gas delivery apparatus.

11. A method for monitoring delivery of additive gas to a patient by means of an additive gas delivery apparatus, comprising:

determining, by a computer of the additive gas delivery apparatus, if a monitored parameter indicates that the patient is connected to the additive gas delivery apparatus;

determining, by said computer, if the additive gas delivery apparatus is in a passive state in which it does not deliver additive gas; and activating, by said computer, an alarm if said monitored parameter indicates that the patient is connected to the additive gas delivery apparatus when in said passive state.

12. The method according to claim 11, wherein the determination as to whether the additive gas delivery apparatus is in said passive state comprises determination of a current operational mode of the additive gas delivery apparatus.

13. The method according to claim 12, wherein the determination of the current operational mode of the additive gas delivery apparatus comprises determination of a software parameter indicative of said current operational mode.

14. The method according to claim 13, further comprising:

receiving user input indicative of a desired change in operational mode of said additive gas delivery apparatus;

changing, based on said desired change in operational mode, at least one operational parameter of the additive gas delivery apparatus in order to put the apparatus into a new operational mode; and setting said software parameter to a value indicative of said new operational mode.

15. The method according to claim 11, wherein the monitored parameter indicative of whether the patient is connected to the additive gas delivery apparatus relates to a flow and/or pressure indicative of spontaneous, supported or controlled breathing activity of the patient.

* * * * *